United States Patent
Dang et al.

(10) Patent No.: US 10,229,288 B2
(45) Date of Patent: Mar. 12, 2019

(54) ENHANCED DATA SECURITY PLATFORM

(71) Applicant: International Business Machines Corporation, Armonk, NY (US)

(72) Inventors: Bing Dang, Chappaqua, NY (US); John U. Knickerbocker, Monroe, NY (US); Minhua Lu, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 207 days.

(21) Appl. No.: 15/156,800

(22) Filed: May 17, 2016

(65) Prior Publication Data
US 2017/0337392 A1    Nov. 23, 2017

(51) Int. Cl.
| | | |
|---|---|---|
| G06F 21/00 | (2013.01) | |
| G06F 21/62 | (2013.01) | |
| G06F 19/00 | (2018.01) | |
| G06F 21/32 | (2013.01) | |
| H04L 29/06 | (2006.01) | |
| G06F 21/60 | (2013.01) | |

(52) U.S. Cl.
CPC .......... *G06F 21/6245* (2013.01); *G06F 19/00* (2013.01); *G06F 19/324* (2013.01); *G06F 21/32* (2013.01); *G06F 21/602* (2013.01); *H04L 63/0861* (2013.01)

(58) Field of Classification Search
None
See application file for complete search history.

(56) References Cited

U.S. PATENT DOCUMENTS

| | | |
|---|---|---|
| 7,593,549 B2 | 9/2009 | Reiner |
| 8,170,609 B2 | 5/2012 | Hedtke et al. |
| 8,447,273 B1 | 5/2013 | Friedlander et al. |
| 8,670,998 B2 | 3/2014 | Bertha et al. |

(Continued)

OTHER PUBLICATIONS

L. Wang et al., "Medical Applications and Healthcare Based on Cloud Computing," International Journal of Cloud Computing and Services Science (IJ-CLOSER), Aug. 2014, pp. 217-225, vol. 2, No. 4.

*Primary Examiner* — Eleni A Shiferaw
*Assistant Examiner* — Andrew J Steinle
(74) *Attorney, Agent, or Firm* — L. Jeffrey Kelly; Ryan, Mason & Lewis, LLP (57) ABSTRACT

A method for providing data security comprises operatively connecting sensing elements with a user, sensing characteristics of the user via the sensing elements, wherein each of the sensing elements comprises at least one unique semiconductor identifier. The at least one unique semiconductor identifier and data concerning the sensed characteristics is transmitted from the sensing elements to a data analytics engine, and at least one unique biological identifier associated with the user is attached to the transmission of the at least one unique semiconductor identifier and the data concerning the sensed characteristics. The method further includes verifying by the data analytics engine that the at least one unique semiconductor identifier of the sensing elements and the at least one biological identifier are valid, analyzing by the data analytics engine the data concerning the sensed characteristics, and generating and transmitting a response based on the analysis.

20 Claims, 6 Drawing Sheets

(56) References Cited

U.S. PATENT DOCUMENTS

| | | |
|---|---|---|
| 8,679,012 B1 | 3/2014 | Kayyali |
| 2007/0197881 A1 | 8/2007 | Wolf et al. |
| 2010/0137693 A1 | 6/2010 | Porras et al. |
| 2011/0040574 A1* | 2/2011 | Fung ............... A61B 5/0205 705/2 |
| 2013/0076531 A1* | 3/2013 | San Vicente ...... A61B 5/0015 340/870.02 |
| 2013/0210360 A1* | 8/2013 | Ljung ............... H04M 1/7253 455/41.2 |
| 2013/0262155 A1 | 10/2013 | Hinkamp |
| 2014/0236249 A1 | 8/2014 | Rao et al. |
| 2014/0244296 A1 | 8/2014 | Linn et al. |
| 2014/0257833 A1 | 9/2014 | Williams |
| 2014/0337221 A1* | 11/2014 | Hoyos ............... H04L 63/0861 705/44 |
| 2015/0037781 A1* | 2/2015 | Breed ............... G09B 7/00 434/362 |

\* cited by examiner

PILL

*FIG. 2B*

PATCH

*FIG. 2C*

CONTACT LENS

*FIG. 2D*

PART OF GLASSESS

*FIG. 2E*

MICROSYSTEM

ENHANCED DATA SECURITY PLATFORM

TECHNICAL FIELD

The field generally relates to providing data security and, in particular, to providing an enhanced data security platform that makes use of a combination or subset of semiconductors, unique tags or numbers, biological markers, a software program, a time management system and/or an encryption system.

BACKGROUND

Given network and digital platforms for storing and accessing data, the security and protection of such data has become an issue of major importance. For example, data including, but not necessarily limited to, medical, financial (e.g., bank and credit card accounts), social security, and personal data, personal healthcare records, can be at risk of being compromised due to, for example, security system malfunctions and/or security breaches caused by online and/or wireless hacking. In addition, system errors can result in data associated with one party being incorrectly linked to another party.

As is known, when private or secure data is compromised or incorrectly associated with the wrong party, the results can be catastrophic. For example, security breaches can be life threatening in the case of medical data, resulting in wrongful healthcare actions based on data that is not linked to the appropriate persons or data that is accessed by unauthorized individuals with malicious intent. Security breaches can also be costly if access to assets, such as bank data or other financial data, are compromised. In some cases, security lapses connected to one or more individuals can lead to problems with one or more family members of the compromised individual, such as spouses and children.

Security measures exist, such as, for example, encryption and/or password identification. However, additional and/or improved security measures are needed to ensure adequate protection of data as security breaches become increasingly likely due to more sophisticated hacking techniques.

SUMMARY

According to an exemplary embodiment of the present invention, a method for providing data security comprises operatively connecting one or more sensing elements with a user, sensing one or more characteristics of the user via the one or more sensing elements, wherein each of the one or more sensing elements comprises at least one unique semiconductor identifier, transmitting the at least one unique semiconductor identifier and data concerning the one or more sensed characteristics from the one or more sensing elements to a data analytics engine, attaching at least one unique biological identifier associated with the user to the transmission of the at least one unique semiconductor identifier and the data concerning the one or more sensed characteristics, verifying by the data analytics engine that the at least one unique semiconductor identifier of the one or more sensing elements and the at least one biological identifier are valid, analyzing by the data analytics engine the data concerning the one or more sensed characteristics, generating a response based on the analysis, and transmitting the response from the data analytics engine to an integration device associated with the user.

According to an exemplary embodiment of the present invention, a system for data security comprises a memory and at least one processor coupled to the memory, wherein the at least one processor is configured to receive data concerning one or more sensed characteristics of a user from one or more sensing elements operatively connected with the user, wherein each of the one or more sensing elements comprises at least one unique semiconductor identifier, transmit the at least one unique semiconductor identifier of the one or more sensing elements and the data concerning the one or more sensed characteristics to a data analytics engine, attach at least one unique biological identifier associated with the user to the transmission of the at least one unique semiconductor identifier and the data concerning the one or more sensed characteristics, verify that the at least one unique semiconductor identifier of the one or more sensing elements and the at least one biological identifier are valid, analyze the data concerning the one or more sensed characteristics, and generate and transmit a response based on the analysis.

According to an exemplary embodiment of the present invention, a computer program product for providing data security comprises a computer readable storage medium having program instructions embodied therewith, the program instructions executable by a processor to cause the processor to perform a method comprising receiving data concerning one or more sensed characteristics of a user from one or more sensing elements operatively connected with the user, wherein each of the one or more sensing elements comprises at least one unique semiconductor identifier, transmitting the at least one unique semiconductor identifier of the one or more sensing elements and the data concerning the one or more sensed characteristics to a data analytics engine, attaching at least one unique biological identifier associated with the user to the transmission of the at least one unique semiconductor identifier and the data concerning the one or more sensed characteristics, verifying that the at least one unique semiconductor identifier of the one or more sensing elements and the at least one biological identifier are valid, analyzing the data concerning the one or more sensed characteristics, and generating and transmitting a response based on the analysis.

These and other exemplary embodiments of the invention will be described or become apparent from the following detailed description of exemplary embodiments, which is to be read in connection with the accompanying drawings.

BRIEF DESCRIPTION OF THE DRAWINGS

Exemplary embodiments of the present invention will be described below in more detail, with reference to the accompanying drawings, of which.

DETAILED DESCRIPTION

Exemplary embodiments of the invention will now be discussed in further detail with regard data security and, in particular, to providing an enhanced data security platform using a combination or subset of semiconductors, unique tags (e.g., radio-frequency identification (RFID)) or numbers, biological markers, a software program, a time management system and/or an encryption system. This invention may, however, be embodied in many different forms and should not be construed as limited to the embodiments set forth herein.

As used herein, the term "real-time" refers to output within strict time constraints. Real-time output can be understood to be instantaneous or in the order of milliseconds or microseconds. Of course, it should be understood that depending on the particular temporal nature of the system in which an embodiment of the invention is implemented, other appropriate timescales that provide at least contemporaneous performance and output can be achieved.

As used herein, an "ad hoc network" or "wireless ad hoc network (WANET)" can refer to a decentralized type of wireless network that does not rely on a pre-existing infrastructure, such as routers or access points in managed (e.g., infrastructure) wireless networks. As used herein, an ad hoc network or WANET can be a self-configuring, dynamic network that lacks infrastructure setup and administration, enabling devices to independently create and join the network.

As used herein, a "managed type" of network, can refer to, but is not necessarily limited to, a local area network (LAN), wide area network (WAN), cellular network, satellite network or the Internet. The communication can be performed via one or more centralized servers or cloud data centers that receive, analyze and send data to and from smart phones, wearable sensors and/or wearable computing eyeglasses that, by way of example, are part of the network.

The network communications can be based on relatively close-range communication capabilities, such as, for example, BLUETOOTH and/or near field communication (NFC) capabilities. The embodiments of the present invention are not necessarily limited to BLUETOOTH and/or NFC protocols, and can include other relatively close or longer range protocols, such as, for example, IEEE 802.11, radio-frequency identification (RFID), WiFi, cellular and satellite protocols.

As used herein, a "semiconductor identifier," "semiconductor tag," "chip identifier," or "chip tag" can refer to a label corresponding to an object, such as a chip in a device, to be identified. The label can include, for example, a unique tag serial number, and/or may include product-related information such as stock number, lot or batch numbers, production dates, or other specific information. According to an embodiment of the present invention, the label and other information can be encrypted.

As used herein, an "RFID tag" can refer to the combination of an integrated circuit for storing and processing information, modulating and demodulating a radio-frequency (RF) signal, collecting DC power from the incident reader signal, and an antenna for receiving and transmitting the signal. Two-way radio frequency transceivers, called interrogators or readers, send a signal to the RFID tag and read its response including the identifying label and possibly other information.

In accordance with an embodiment of the present invention, a smart life enhancement system provides for integration of hardware, software and analysis of electronic information from and to one or more persons having an electronic component or device. The electronic information is communicated from and to the electronic component or device within the a local smart system or between the local smart system and other electronic systems, which may be remote from the local smart system, such as, but not necessarily limited to, private, secured and/or public systems, such as analytical, cloud, medical and/or business systems, using, for example, electronic, optical, wireless, and/or wired connections.

According to an embodiment of the present invention, the local smart system can include one or more on- or in-person components capable of one- or two-way communication with the one or more on- or in-person sensors including an energy source, a sensing element, and a processor for local data analysis, and control of data for collection, storage, analysis and communication. Such controls may include, for example, communication type and timing, security and/or encryption, identification of sensor users, identification of transmitting and/or receiving devices, timing of sensing, power management, and addresses and authorization of secure receivers of data.

In accordance with an embodiment of the present invention, data is transferred to one or more smart integration devices possessed by a user from one or more of the sensors. An integration device can be configured to review data from one or more of the sensors, and analyze and compare the sensor data relative to reference data. The reference data can include, for example, lower and upper normal reference ranges of the data against any one or more types of data being collected such as, but not limited to, body characteristics like heart rate, temperature, glucose level, blood pressure, oxygen level, ion level(s), $CO_2$ level, $N_2$ level, alcohol level, disease level, radiation level, acceleration level, position (e.g., standing/vertical or laying down/horizontal), stress level, or other sensing or diagnostic data. In addition, the reviewed and/or analyzed data can be transferred from one or more of the integration devices to one or more electronic components for potential communication with another person, or computing device that may provide a response with information of value to regarding appropriate actions to be taken based on the data derived from the sensors, and/or knowledge gained from the sensor data.

According to an embodiment of the present invention, data security, for data including, but not necessarily limited to, health and financial data, can be achieved with the use of one or more of personal biometric and/or bio-genetic data, including DNA or partial DNA, RNA, secure chip identifiers or tags, such as RFID tags, including RFID tags on implantable devices, passwords, and encryption.

Figure 1:
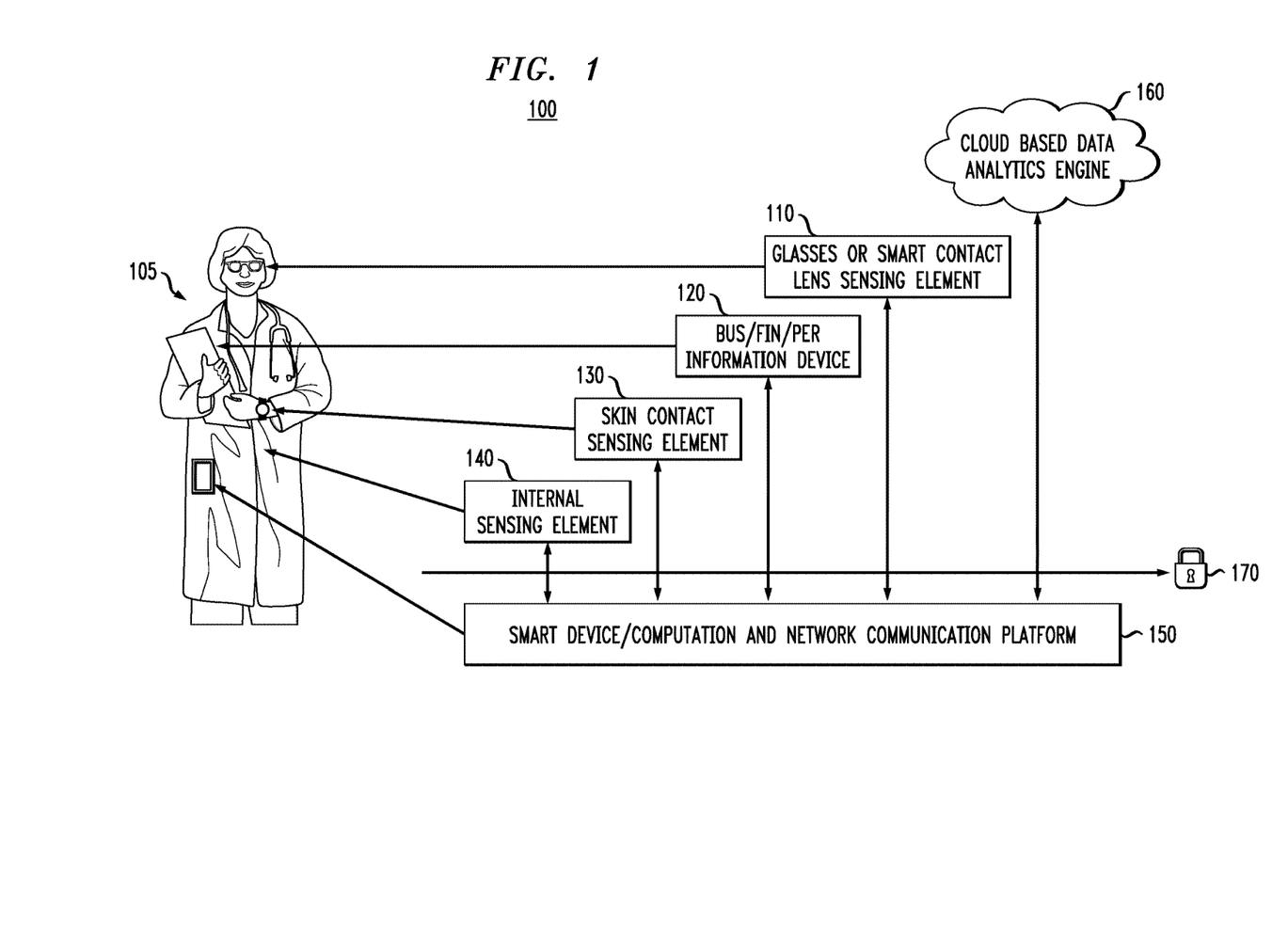
FIG. 1 is a block diagram of a system for providing data security, according to an exemplary embodiment of the present invention.

FIG. 1 is a block diagram of a system for providing data security, according to an exemplary embodiment of the present invention. As shown in FIG. 1 by lines and/or arrows, the components of the system 100 are operatively coupled to each other via, for example, physical connections, such as wired and/or direct electrical contact connections, and wireless connections, such as, for example, WiFi, BLUETOOTH, IEEE 802.11, and/or networks, including but not limited to, a LAN, WAN, cellular network, ad hoc networks, WANET, satellite network or the Internet.

By way of non-limiting example, in accordance with an embodiment of the present invention, referring to FIG. 1, an individual or user 105 is equipped with one or more sensing elements 110, 130 and 140. For example, the sensing elements include, but are not necessarily limited to, an eyeglasses or contact lens sensing element 110, a skin contact sensing element 130, such as a watch or patch, and an internal sensor 140, such as an implantable sensor, or a sensor that is able to be swallowed, such as one embedded in a pill or capsule. Implantable or ingestible devices can be set to be operational for a predetermined time period and can be replaceable and updated when the predetermined time period expires.

As can be seen in connection with FIGS. 2A-2D, which are diagrams illustrating sensing elements used in connection with a system for providing data security, according to exemplary embodiments of the present invention, each of a pill sensing element 210, a patch sensing element 220, a contact lens sensing element 230, and an eyeglasses sensing element 240 can include a sensing portion 212, 222, 232, 242, an energy/power source 214, 224, 234, 244 and a processor 216, 226, 236, 246, such as, for example, a microprocessor. The sensing elements 210, 220, 230 and/or 240 can each include a low power microelectromechanical system (MEMS) comprising, for example, a self-contained and integrated sensor, a microprocessor, communication components for receiving and transmitting data, and an integrated energy source/harvester. The sensing elements have a small form factor and can be disposable, as well as, in the case of ingestible sensing elements, such as pills or capsules, being easy to ingest.

As noted above, the processor of a sensing element can be used for local data analysis. As noted above, sensing elements can collect data such as, but not limited to, body characteristics like heart rate, temperature, glucose level, blood pressure, oxygen level, ion level(s), $CO_2$ level, $N_2$ level, alcohol level, disease level, radiation level, acceleration level, position (e.g., standing/vertical or laying down/horizontal), and stress level.

The processor of a sensing element also controls collection, storage, analysis and communication of data determining, for example, communication type, including, but not necessarily limited to, RF, electric, and optical communication and wireless protocols, timing of the communications, and how communications can be secured (e.g., encryption). The processors 216, 226, 236 and 246 can control identification of sensor users, and of devices with which the sensing elements are communicating (e.g., device tag identification), timing of sensing, power management, and addresses and authorization of secure receivers of data. The processors 216, 226, 236, 246 can also control functionality associated with receiving chip identifier interrogations and transmission of chip identifiers.

Referring to FIG. 1, the system 100 also includes a business/financial/personal information device 120 of the user 105. The business, financial and personal information device 120 can be, for example, a computing device, such as a personal computer, notebook computer, tablet or mobile phone, and includes proprietary business, financial or personal information (e.g., health information) one or more individuals or entities.

Data is transferred from the sensing elements 110, 130 and 140, and/or from the business, financial and personal information device 120 to one or more smart integration devices 150 possessed by a user 105 using, for example, physical connections, such as wired and/or direct electrical contact connections, or wireless connections, such as, for example, NFC, WiFi, BLUETOOTH, IEEE 802.11, and/or networks, including but not limited to, a LAN, WAN, cellular network, ad hoc networks, WANET, satellite network or the Internet. The integration device 150 can be, for example, a smart computing device, such as a mobile phone or tablet capable of two-way communication with the elements 110-140, as well with a cloud based data analytics engine 160. The integration device 150 can be configured to review data from one or more of the elements 110-140, analyze and compare the data relative to reference data, and provide responses regarding appropriate actions to be taken based on the data.

In accordance with an embodiment of the present invention, in addition to the integration device 150, the cloud based data analytics engine 160 provides responses with information of value to initiators or other parties associated with the initiators based on the data from the sensing elements 110, 130 and 140, and/or from the business, financial and personal information device 120. For example, in the case of medical data indicating a serious condition of users having the sensing elements 110, 130 and 140, the response may include instructions on what medication or actions to take based on the user's condition. In addition to the integration devices 150, the cloud based data analytics engine 160 can be configured to review the data from the sensing elements 110, 130 and 140, and/or from the business, financial and personal information device 120, analyze and compare the data relative to reference data, and provide a response with information of value regarding appropriate actions to be taken based on the data. The reference data may include, for example, historical baseline data of a user, and/or data of others that may be of defined parametrics, such as, for example, similar genetics, to be considered relevant to a particular user. The response can include actionable messaging to a user 105, to user designated persons (e.g., doctors, family members) or user designated systems including recommendations, preventive actions against chronic disease and cancer, diagnostic or life-saving measures to be taken. Given the sensitivity and importance of the responses, embodiments of the present invention provide real-time analysis of data and provision of responses with information of value to reach the appropriate users or entities in real-time over one or more of the communication networks described herein. In a non-limiting example, such responses can be useful for a user 105 equipped with sensing elements 110, 130, 140 who was released from a hospital, or has a long-term health condition. In this case, the user's health can be securely evaluated, and any changes away from a normal range of the sensed data can be securely addressed in real-time by automated instructions or from instructions from authorized healthcare professionals having access to the sensed information via the integration device 150 and/or the cloud based data analytics engine 160.

The cloud based data analytics engine 160 can also provide remote storage of data, control timing of retrieval and measurement of data from the integration devices 150 or elements 110-140. The integration devices 150 and/or the cloud based data analytics engine 160 can also store the data to be used as reference data to identify trending or actionable limits of a user to be used when deciding whether to take action on particular data received. For example, in the case of financial data, if withdrawals or spending of user are exceeding routine limits, action may be taken to suspend account activity.

In accordance with embodiments of the present invention, analysis and review of data from elements 110-140 to provide responses of value can also be performed by the elements 110-140 and the responses can be provided to the integration devices 150.

The system 100 provides for improved security measures/protocols 170 in connection with the transfer of data in the system 100. As can be seen in FIG. 1 by the double-sided arrows, two-way data transfer is provided between elements 110-140 and integration device 150, and between integration device 150 and cloud based data analytics engine 160. Although not shown, secure communication can also be between elements 110-140 themselves, and between elements 110-140 and cloud based data analytics engine 160. In accordance with embodiments of the present invention, improved security measures/protocols 170 are used to prevent the data from being compromised or incorrectly associated with the wrong party. Such security measures/protocols 170 include, for example, verifying communication sources or recipients using encryption keys for encrypted data communications, personal identification marker(s), including, for example, biological identifiers, such as personal biometric data and bio-genetic data, password enhancement, including, for example, varying timing of validity of passwords, and/or secure chip tags, such as RFID tags, and any combination thereof. Personal biometric data and bio-genetic data, includes, but is not necessarily limited to, DNA or partial DNA of users, data in body fluids (e.g., blood, sweat, tears), and unique body data, such as, for example, fingerprint data, hand geometry, earlobe geometry, retina and iris patterns, and/or voice waves. The elements 110-140, 210-240, the integration device 150 and the cloud based data analytics engine 160 may be programmed with a user's personal identification marker(s) and/or the sensing elements 110, 130, 140, 210-240 can actively collect personal biometric and bio-genetic data from a user. In accordance with an embodiment of the present invention, secure chip tags may dynamically update, and may include encrypted codes for a chip or chipset.

Information can be controlled using the above noted security measures/protocols 170 in wired or wireless communications by and between elements 110-140, integration devices 150, cloud based data analytics engines 160, and devices used by, for example, health professionals, security agencies, police, relatives, family members or other designated individuals.

In accordance with an embodiment of the present invention, levels of security can be dynamically increased or decreased, and/or pre-designated to be different depending on what is determined to be normal activity, or activity determined to be outside of the normal range of activity, such as, for example, suspected fraudulent spending activity, or body activity, such as heart rate or blood pressure outside of normal limits that may be life threatening.

According to an embodiment of the present invention, the determination of which combinations of security measures/protocols 170 to reference when providing access to or verifying sources and/or recipients of data, can be periodically changed. For example, the determination of which combinations of biometric data to reference when providing access to secure information can change based on timed updates and/or can be dynamically altered without notice during data transmission or as a request for data is being made. As a result, potential hackers are unable to discern a pattern of which security protocols are used and are unable to reuse misappropriated access materials, such as, but not limited to, passwords, biometric data, and encryption keys. The timed updates can be randomly scheduled, so as to avoid any pattern recognition in connection with the altering of which combinations of security measures/protocols 170 to reference when providing access to or verifying sources and/or recipients of data.

Security measures/protocols 170 can also be based on a location of a particular user based on trending positioning system data, such as global positioning system (GPS) data of a user. For example, it may be determined that an individual, such as user 105, is typically at a particular location at designated times, such as, at work during the hours of 9 am to 5 pm. If data or a request for access to secure data is being transmitted from a source purporting to be the user, but the location of the source is not the typical location for that time, it may be determined that there is a problem, such as an emergency causing the user to be in a different place, or a false user attempting to pose as the user. If a problem with security verification or access is determined, the communication can be flagged, access to secure data can be denied in real-time, and/or a real-time alert can be issued to the appropriate individual or entity charged with investigating security breaches.

Communicated data, via, for example, wireless electronic or optical techniques, can be verified from one or more sensing elements, and from smart and/or analytical platforms for the benefit of users and/or associates of users. Referring to FIG. 1, for example, one or more sensing elements 110, 130 and 140 may include secure chip tags, such as RFID tags, and sense or retrieve pre-programmed personal biometric data and bio-genetic data, including, but not necessarily limited to, DNA or partial DNA of users 105, data in body fluids (e.g., blood, sweat, tears), and unique body data, such as, for example, fingerprint data, hand geometry, earlobe geometry, retina and iris patterns, and/or voice waves. In accordance with an embodiment of the present invention, the secure chip tags, and the personal biometric and bio-genetic data is sent to an integration device 150, such as, for example, a smart phone or tablet.

Business, financial and personal information, such as, for example, asset and financial account information, is sent from a business, financial and personal information device 120, such as, for example, a computing device, such as a personal computer, notebook computer, tablet or mobile phone, to the integration device 150. Like the sensing elements 110, 130 and 140, the business, financial and personal information device 120 may include a secure chip tag, such as an RFID tag and/or personal identification marker(s) that are transmitted with the data. In order to keep the data from the sensing elements 110, 130 and 140, and the business, financial and personal information device 120 secure, the integration device 150 associates the data from these components 110-140 with their secure chip tags, and with the personal biometric data and bio-genetic data. Any transmission of data and/or request for access to information from a secure system received from the integration device 150 is accompanied by the secure chip tags and the personal biometric and bio-genetic data, so that such transmissions and/or requests can be verified as coming from a particular user 105. In accordance with an embodiment of the present invention, a semiconductor security solution, for example, a chip tag is coupled with a biological type security solution, for example, biometric and/or bio-genetic data. In addition, as noted above, additional security measures/protocols can be implemented in connection with the transmission of data and requests, including, for example, encrypted data communications, password enhancement, scheduled and dynamic altering of the combinations of security measures/protocols used, and trending positioning system data.

Upon receiving a transmission of data and/or request for access to information, the cloud based data analytics engine 160 or any other system, such as a remote system accessed over a network, can verify, based on the security measures/protocols 170 in place at that time, the identity of sender. By way of non-limiting example, the cloud based data analytics engine 160 or other remote system, can verify that biological or health related information, financial information and/or requests for secure information are coming from a particular user by checking for matches to secure chip tags and personal identification markers, or other security measures/protocols 170 used. If the source is authenticated, the cloud based data analytics engine 160 or other remote system can provide the requested information and/or responses with information of value to the integration device 150. In obtaining the requested information, the cloud based data analytics engine 160 may use the security measures/protocols 170 to obtain access to proprietary health and/or financial information of a user. In addition, like the cloud based data analytics engine 160 or other remote system, the integration device 150 can verify that received data comes from a particular source by checking for matches to secure chip tags and personal identification markers associated with the data. Further, given the nature of information received from the integration device 150, the cloud based data analytics engine 160 may issue one or more alerts to authorized individuals, including the user, concerning the health of a user and remedial actions to take if a problem is identified. Also, as noted above, if there is a problem with security verification or access based on one or more of the security measures/protocols 170 not being satisfied, the communication can be flagged, access to secure data can be denied in real-time, and/or a real-time alert can be issued to the appropriate individual or entity charged with investigating security breaches.

Figure 2A:
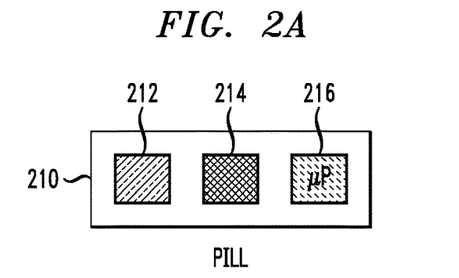
FIGS. 2A-2D are diagrams illustrating sensing element used in connection with a system for providing data security, according to an exemplary embodiments of the present invention.
Figure 2B:
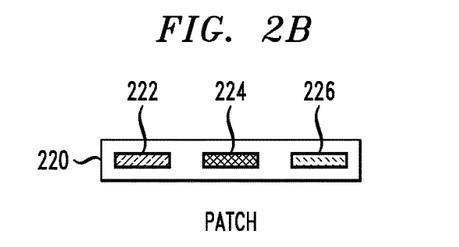
Figure 2C:
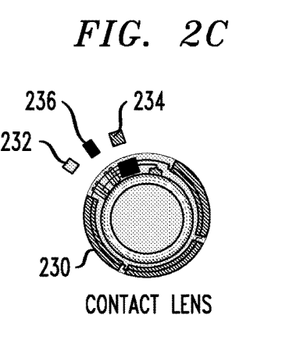
Figure 2D:
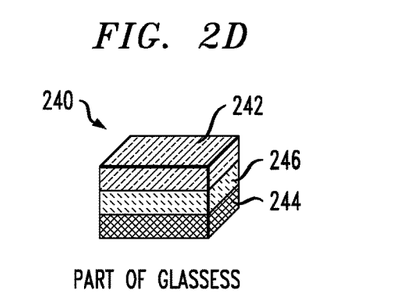
Figure 2E:
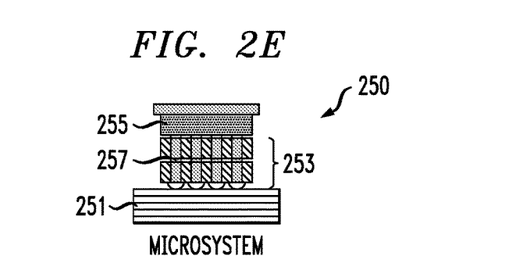
FIG. 2E is a diagram illustrating a cross-section of a microsystem used in connection with a system for providing data security, according to an exemplary embodiment of the present invention.

FIG. 2E is a diagram illustrating a cross-section of a microsystem used in connection with a system for providing data security, in accordance with an exemplary embodiment of the present invention. The microsystem 250 can be part of a sensing element 110, 130, 140, 210-240, a business, financial and personal information device 120, and/or the integration device 150. The microsystem 250 includes a base package 251, processor, memory and other functioning chips 253, and a secure chip 255 from which a secure chip tag, such as an encrypted RFID tag, is derived. Contact vias 257 can run between the chips 255 and 253 to the base package 251. The processor, memory and other functioning chips 253 provide analysis functionality to, for example, analyze sensed data or verify communication partners, and control transmission and reception of data with other devices or platforms, such as the cloud based data analytics engine 160 or local devices of the system 100.

Figure 3:
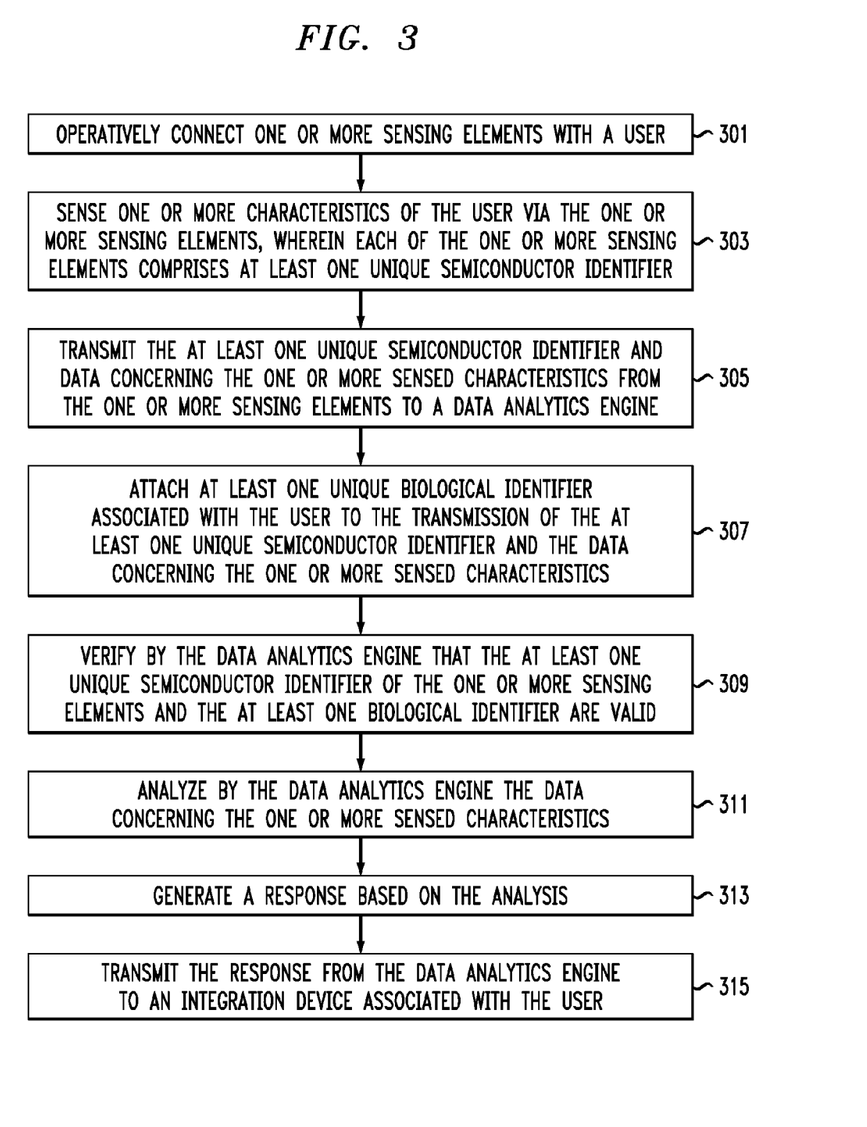
FIG. 3 is a flow diagram of a process for providing data security, according to an exemplary embodiment of the invention.

FIG. 3 is a flow diagram of a process for providing data security, according to an exemplary embodiment of the invention. Referring to FIG. 3, the process 300 includes, at block 301, operatively connecting one or more sensing elements with a user. Operatively connecting the one or more sensing elements with the user includes, for example, contacting the one or more sensing elements with a body of the user and/or positioning (e.g., by implantation or ingestion) the one or more sensing elements in the body of the user. At block 303, the process 300 further includes sensing one or more characteristics of the user via the one or more sensing elements. The sensed characteristics can include body characteristics of the user, such as, for example, heart rate, temperature, glucose level, blood pressure, oxygen level, ion level(s), $CO_2$ level, $N_2$ level, alcohol level, disease level, radiation level, acceleration level, position (e.g., standing/vertical or laying down/horizontal), and stress level. Each of the one or more sensing elements comprises at least one unique semiconductor identifier, such as, for example, an encrypted chip identifier, or an identifier used in connection with an RFID tag.

At block 305, the at least one unique semiconductor identifier and data concerning the one or more sensed characteristics is transmitted from the one or more sensing elements to a data analytics engine, which can be a cloud based analytics engine. The transmission can be via an integration device (e.g., a smart phone or a smart tablet) associated with the user. At block 307, at least one unique biological identifier associated with the user is attached to the transmission of the at least one unique semiconductor identifier and the data concerning the one or more sensed characteristics. The unique biological identifier can include, for example, a personal identification marker, such as DNA, partial DNA, data derived from a body fluid, and/or unique body data, such as, for example, fingerprint data, hand geometry, earlobe geometry, retina and iris patterns, and/or voice waves.

At block 309, the data analytics engine verifies that the at least one unique semiconductor identifier of the one or more sensing elements and the at least one biological identifier are valid. Such verification can also be performed by the integration device, or other device or platform in communication with the sensing elements, business, financial and personal information device and/or the integration device. In accordance with an embodiment of the present invention, the verification can further include a timing verification element to verify which identifiers are to be utilized at a particular time, and whether the correct identifiers are being used for the particular time.

At blocks 311, 313 and 315, respectively, the data analytics engine analyzes the data concerning the one or more sensed characteristics, generates a response based on the analysis, and transmits the response from the data analytics engine to an integration device associated with the user. In accordance with an embodiment of the present invention, the transmission is performed using encryption techniques. The analysis and generation of a response can alternatively be performed by the integration device, or other device or platform in communication with the sensing elements, business, financial and personal information device and/or the integration device.

Analyzing the data concerning the one or more sensed characteristics can include a comparison of the data concerning the one or more sensed characteristics with reference data, and determining whether the data concerning the one or more sensed characteristics falls outside of a range in the reference data indicating, for example, a potential problem, such as a health concern requiring immediate attention. Based on the results of the analysis, the response can include a real-time alert upon determining that the data concerning the one or more sensed characteristics falls outside of the range in the reference data, and an emergent situation exists.

According to an embodiment, there may be a plurality of unique biological identifiers associated with the user. In order to enhance security, the process can include dynamically altering which of the plurality of unique biological identifiers are referenced when verifying validity of the at least one unique biological identifier. As a result, potential hackers are unable to discern a pattern of which security protocols are used and are unable to reuse misappropriated access materials, such as, but not limited to, the unique biological identifiers. Similarly, the unique semiconductor identifier(s) of the one or more sensing elements can be dynamically updated.

According to an embodiment, the process 300 can further include generating a request for data from the integration device, transmitting the request for data from the integration device to the data analytics engine with at least one unique semiconductor identifier corresponding to the integration device, and attaching at least one unique biological identifier associated with the user to the transmission of the request for data. A data analytics engine can verify that the unique semiconductor identifier corresponding to the integration device and the biological identifier are valid, and using trends in positioning system data associated with the user to verify that the request for data from the integration device is valid. For example, if it is determined that a user is typically at a particular location at designated times, and data or a request for access to secure data is being transmitted from a source purporting to be the user from a location that is not the typical location for that time, it may be determined that there is a problem.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 4:
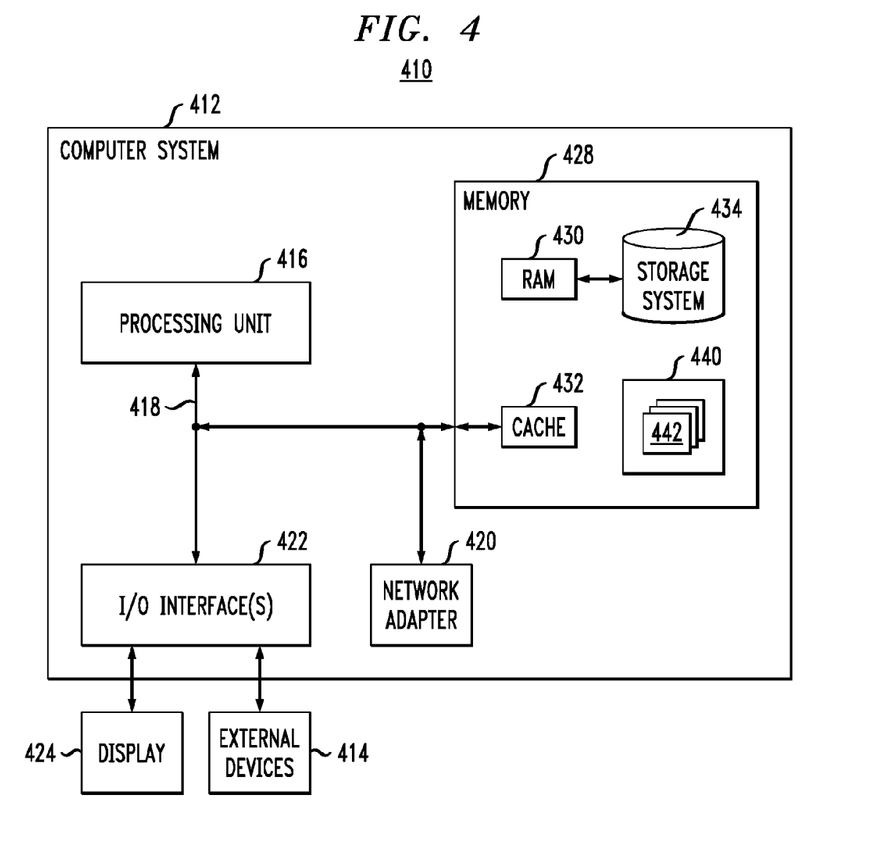
FIG. 4 illustrates a computer system in accordance with which one or more components/steps of the techniques of the invention may be implemented, according to an exemplary embodiment of the invention.

One or more embodiments can make use of software running on a general-purpose computer or workstation. With reference to FIG. 4, in a computing node 410 there is a computer system/server 412, which is operational with numerous other general purpose or special purpose computing system environments or configurations. Examples of well-known computing systems, environments, and/or configurations that may be suitable for use with computer system/server 412 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 412 may be described in the general context of computer system executable instructions, such as program modules, being executed by a computer system. Generally, program modules may include routines, programs, objects, components, logic, data structures, and so on that perform particular tasks or implement particular abstract data types. Computer system/server 412 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 412 in computing node 410 is shown in the form of a general-purpose computing device. The components of computer system/server 412 may include, but are not limited to, one or more processors or processing units 416, a system memory 428, and a bus 418 that couples various system components including system memory 428 to processor 416.

The bus 418 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 412 typically includes a variety of computer system readable media. Such media may be any available media that is accessible by computer system/server 412, and it includes both volatile and non-volatile media, removable and non-removable media.

The system memory 428 can include computer system readable media in the form of volatile memory, such as random access memory (RAM) 430 and/or cache memory 432. The computer system/server 412 may further include other removable/non-removable, volatile/nonvolatile computer system storage media. By way of example only, storage system 434 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 418 by one or more data media interfaces. As depicted and described herein, the memory 428 may include at least one program product having a set (e.g., at least one) of program modules that are configured to carry out the functions of embodiments of the invention. A program/utility 440, having a set (at least one) of program modules 442, may be stored in memory 428 by way of example, and not limitation, as well as an operating system, one or more application programs, other program modules, and program data. Each of the operating system, one or more application programs, other program modules, and program data or some combination thereof, may include an implementation of a networking environment. Program modules 442 generally carry out the functions and/or methodologies of embodiments of the invention as described herein.

Computer system/server 412 may also communicate with one or more external devices 414 such as a keyboard, a pointing device, a display 424, etc., one or more devices that enable a user to interact with computer system/server 412, and/or any devices (e.g., network card, modem, etc.) that enable computer system/server 412 to communicate with one or more other computing devices. Such communication can occur via Input/Output (I/O) interfaces 422. Still yet, computer system/server 412 can communicate with one or more networks such as a local area network (LAN), a general wide area network (WAN), and/or a public network (e.g., the Internet) via network adapter 420. As depicted, network adapter 420 communicates with the other components of computer system/server 412 via bus 418. It should be understood that although not shown, other hardware and/or software components could be used in conjunction with computer system/server 412. Examples, include, but are not limited to: microcode, device drivers, redundant processing units, external disk drive arrays, RAID systems, tape drives, and data archival storage systems, etc.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Computing node 410 in FIG. 4 can be an example of a cloud computing node. Computing node 410 is only one example of a suitable cloud computing node and is not intended to suggest any limitation as to the scope of use or functionality of embodiments of the invention described herein. Regardless, computing node 410 is capable of being implemented and/or performing any of the functionality set forth hereinabove. It is also to be understood that computing node 410 is not necessarily a cloud computing node.

Figure 5:
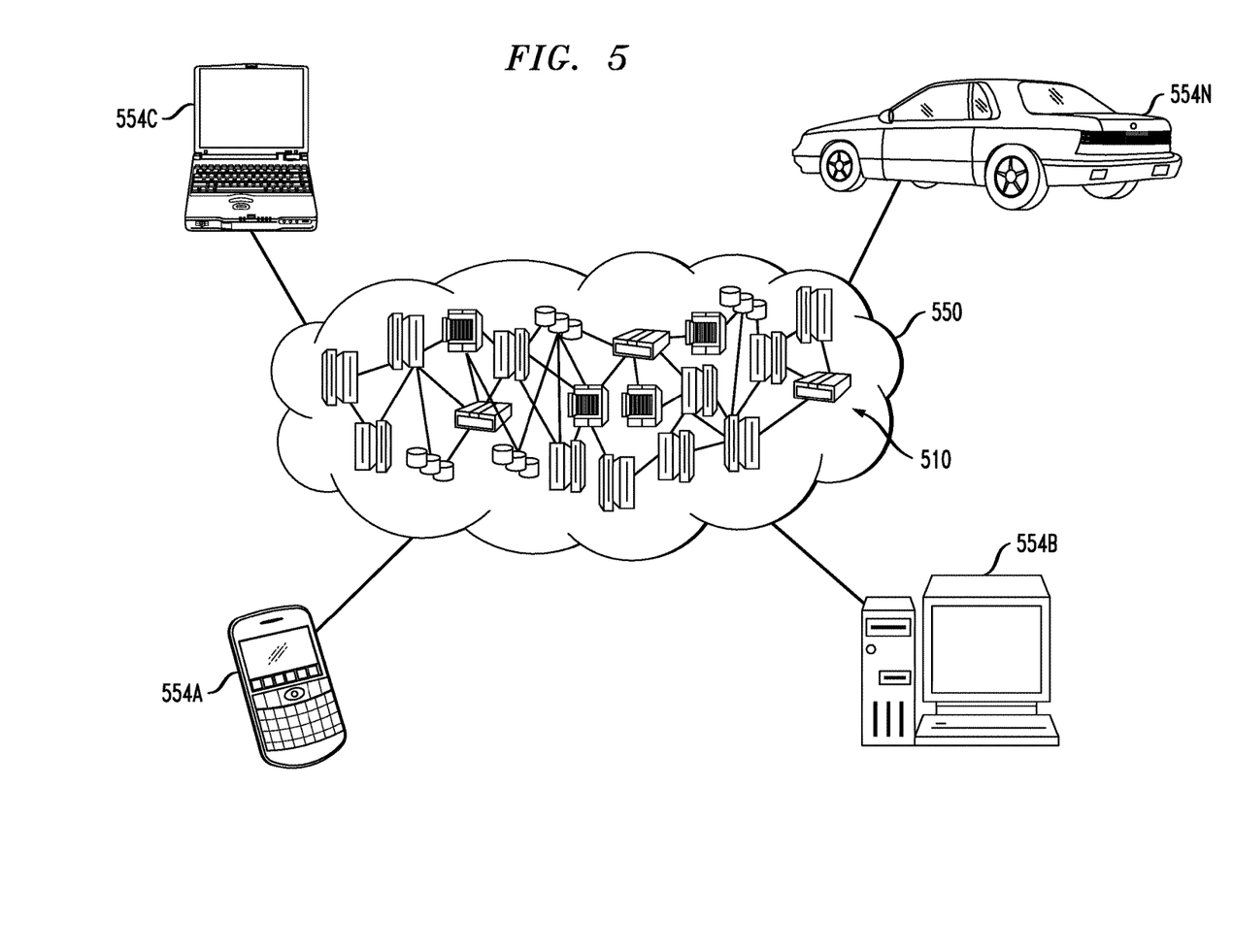
FIG. 5 depicts a cloud computing environment, according to an exemplary embodiment of the present invention.

Referring now to FIG. 5, illustrative cloud computing environment 550 is depicted. As shown, cloud computing environment 550 comprises one or more cloud computing nodes 510 with which local computing devices used by cloud consumers, such as, for example, a wearable device (not explicitly shown), a personal digital assistant (PDA) or cellular telephone 554A, desktop computer 554B, laptop computer 554C, and/or automobile computer system 554N may communicate. Nodes 510 may communicate with one another. They may be grouped (not shown) physically or virtually, in one or more networks, such as Private, Community, Public, or Hybrid clouds as described hereinabove, or a combination thereof. This allows cloud computing environment 550 to offer infrastructure, platforms and/or software as services for which a cloud consumer does not need to maintain resources on a local computing device. It is understood that the types of computing devices 554A-N shown in FIG. 5 are intended to be illustrative only and that computing nodes 510 and cloud computing environment 550 can communicate with any type of computerized device over any type of network and/or network addressable connection (e.g., using a web browser).

Figure 6:
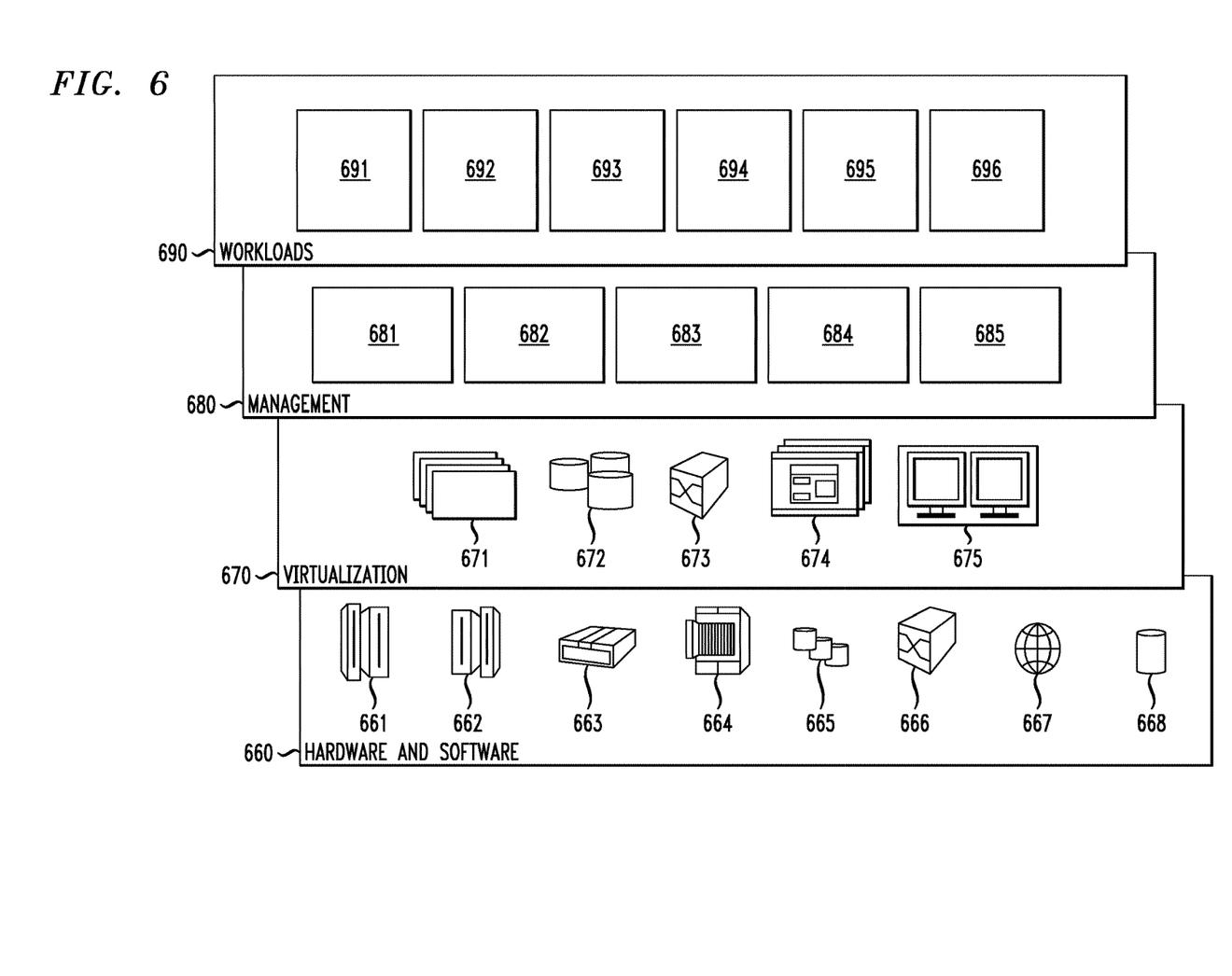
FIG. 6 depicts abstraction model layers, according to an exemplary embodiment of the invention.

Referring now to FIG. 6, a set of functional abstraction layers provided by cloud computing environment 550 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 660 includes hardware and software components. Examples of hardware components include: mainframes 661; RISC (Reduced Instruction Set Computer) architecture based servers 662; servers 663; blade servers 664; storage devices 665; and networks and networking components 666. In some embodiments, software components include network application server software 667 and database software 668.

Virtualization layer 670 provides an abstraction layer from which the following examples of virtual entities may be provided: virtual servers 671; virtual storage 672; virtual networks 673, including virtual private networks; virtual applications and operating systems 674; and virtual clients 675.

In one example, management layer 680 may provide the functions described below. Resource provisioning 681 provides dynamic procurement of computing resources and other resources that are utilized to perform tasks within the cloud computing environment. Metering and Pricing 682 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 683 provides access to the cloud computing environment for consumers and system administrators. Service level management 684 provides cloud computing resource allocation and management such that required service levels are met. Service Level Agreement (SLA) planning and fulfillment 685 provide pre-arrangement for, and procurement of, cloud computing resources for which a future requirement is anticipated in accordance with an SLA.

Workloads layer 690 provides examples of functionality for which the cloud computing environment may be utilized. Examples of workloads and functions which may be provided from this layer include: mapping and navigation 691; software development and lifecycle management 692; virtual classroom education delivery 693; data analytics processing 694; transaction processing 695; and secure data analytics 696, which may implement the functionality described above with respect to FIGS. 1-5.

According to an exemplary embodiment of the present invention, a system for data security comprises a storage or memory component and at least one processor coupled to the storage or memory component, wherein the at least one processor is configured to be an identification verification checkpoint with a unique semiconductor verifier, an encoding and decoding system for encrypted communications to and from a device or the system, and with the ability to check validity of appropriate biological markers and verify time stamps or other identifiers.

According to an exemplary embodiment of the present invention, a computer program product for providing data security comprises a computer readable storage medium having program instructions embodied therewith, the program instructions executable by a processor to cause the processor to perform one or more information updates with or without storage or recording, encrypted communication, authorization of and/or data transfer out of a secure system to another system, person and/or actionable recommendations to banks, stores, hospitals, medical professionals, persons and/or other entities where the method of authorization can comprise one or more of the heretofore identified secure authentication requirements. An example of such a secure authorization method could include, but is not necessarily limited to, a secure hardware chip and/or processor that has a minimum or one or more unique identification tags or numbers that can be encrypted, and for which unique number(s) or code(s) are required for authorization success. The unique identification tags or numbers can be combined with one or more unique biometric data elements such as, but not necessarily limited to, fingerprints, facial recognition, DNA, retina identifiers, one or more of data and/or trending from bio-sensors, etc. The unique identification tags or numbers can further be combined with a time stamp identifier which may identify use of one or more of unique identification tags or numbers authorized to be effective at the time of the authorization request, one or more biometric data elements at the time of the request, one or more communication, and/or encryption code/decode methods to be utilized at the time of an authorization request. In addition, the system can be configured to verify and authorize an actionable communication connection source, connection receiver and encryption method based on a totality of system components and/or protocols (e.g., hardware, biometrics, software, encryption, communication, time stamp and/or authorization rules) being accepted, followed and/or verified.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:
1. A method for providing data security, comprising:
operatively connecting one or more sensing elements with a user;
sensing one or more characteristics of the user via the one or more sensing elements, wherein each of the one or more sensing elements comprises at least one unique semiconductor identifier;
transmitting the at least one unique semiconductor identifier and data concerning the one or more sensed characteristics from the one or more sensing elements to a data analytics engine;
attaching a plurality of unique biological identifiers associated with the user to the transmission of the at least one unique semiconductor identifier and the data concerning the one or more sensed characteristics;
verifying by the data analytics engine that the at least one unique semiconductor identifier of the one or more sensing elements and at least one of the plurality of unique biological identifiers are valid;
analyzing by the data analytics engine the data concerning the one or more sensed characteristics;
generating a response based on the analysis;
transmitting the response from the data analytics engine to an integration device associated with the user;
determining at least one activity associated with the user to be anomalous;
dynamically altering which of the plurality of unique biological identifiers are referenced when verifying validity of the at least one of the plurality of unique biological identifiers;
generating a request for data from the integration device;
transmitting the request for data from the integration device to the data analytics engine with at least one unique semiconductor identifier corresponding to the integration device; and
attaching the at least one of the plurality unique biological identifiers associated with the user to the transmission of the request for data so that the data analytics engine can verify the validity of the at least one of the plurality of unique biological identifiers upon receipt of the request for data;
wherein the dynamically altering is automatically performed in response to the determination that the at least one activity is anomalous and is performed without notice to the user during the transmission of the at least one unique semiconductor identifier and the data concerning the one or more sensed characteristics; and wherein the method is performed by at least one computer system comprising at least one memory and at least one processor coupled to the memory.

2. The method according to claim 1, wherein operatively connecting the one or more sensing elements with the user comprises at least one of contacting the one or more sensing elements with a body of the user and positioning the one or more sensing elements in the body of the user.

3. The method according to claim 1, wherein the one or more sensed characteristics comprise body characteristics of the user.

4. The method according to claim 1, wherein the at least one unique semiconductor identifier comprises an encrypted chip identifier.

5. The method according to claim 1, wherein the at least one of the plurality of unique biological identifiers comprises at least one of DNA, partial DNA, RNA, data derived from a body fluid, and unique body data.

6. The method according to claim 1, wherein the transmission of the at least one unique semiconductor identifier and the data concerning the one or more sensed characteristics to the data analytics engine is performed via the integration device.

7. The method according to claim 1, wherein analyzing the data concerning the one or more sensed characteristics comprises comparing the data concerning the one or more sensed characteristics to reference data, and determining whether the data concerning the one or more sensed characteristics falls outside of a range in the reference data.

8. The method according to claim 7, wherein the response comprises a real-time alert upon determining that the data concerning the one or more sensed characteristics falls outside of the range in the reference data.

9. The method according to claim 1, further comprising dynamically updating the at least one unique semiconductor identifier of the one or more sensing elements.

10. The method according to claim 1, wherein the data analytics engine comprises a cloud based data analytics engine.

11. The method according to claim 1, wherein the integration device comprises one of a smart phone and a smart tablet.

12. The method according to claim 1, further comprising:
verifying by the data analytics engine that the at least one unique semiconductor identifier corresponding to the integration device and the at least one biological identifier attached to the transmission of the request for data are valid; and
using trends in positioning system data associated with the user to verify that the request for data from the integration device is valid.

13. A system for providing data security, comprising:
a memory and at least one processor coupled to the memory, wherein the at least one processor is configured to:
receive data concerning one or more sensed characteristics of a user from one or more sensing elements operatively connected with the user, wherein each of the one or more sensing elements comprises at least one unique semiconductor identifier;
transmit the at least one unique semiconductor identifier of the one or more sensing elements and the data concerning the one or more sensed characteristics to a data analytics engine;
attach a plurality of unique biological identifiers associated with the user to the transmission of the at least one unique semiconductor identifier and the data concerning the one or more sensed characteristics;
verify that the at least one unique semiconductor identifier of the one or more sensing elements and at least one of the plurality of unique biological identifiers are valid;
analyze the data concerning the one or more sensed characteristics;
generate and transmit a response based on the analysis;
determine at least one activity associated with the user to be anomalous;
dynamically alter which of the plurality of unique biological identifiers are referenced when verifying validity of the at least one of the plurality of unique biological identifiers;
generate a request for data from an integration device associated with the user;
transmit the request for data from the integration device to the data analytics engine with at least one unique semiconductor identifier corresponding to the integration device; and
attach the at least one of the plurality of unique biological identifiers associated with the user to the transmission of the request for data so that the data analytics engine can verify the validity of the at least one of the plurality of unique biological identifiers upon receipt of the request for data;
wherein the dynamically altering is automatically performed in response to the determination that the at least one activity is anomalous and is performed without notice to the user during the transmission of the at least one unique semiconductor identifier and the data concerning the one or more sensed characteristics.

14. The system according to claim 13, wherein the at least one processor is further configured to dynamically update the at least one unique semiconductor identifier of the one or more sensing elements.

15. The system according to claim 13, wherein the at least one processor is further configured to:
verify that the at least one unique semiconductor identifier corresponding to the integration device and the at least one biological identifier attached to the transmission of the request for data are valid; and
use trends in positioning system data associated with the user to verify that the request for data from the integration device is valid.

16. The system according to claim 13, wherein in analyzing the data concerning the one or more sensed characteristics, the at least one processor is further configured to compare the data concerning the one or more sensed characteristics to reference data, and determine whether the data concerning the one or more sensed characteristics falls outside of a range in the reference data.

17. A computer program product for providing data security, the computer program product comprising a computer readable storage medium having program instructions embodied therewith, the program instructions executable by a processor to cause the processor to perform a method comprising:
receiving data concerning one or more sensed characteristics of a user from one or more sensing elements operatively connected with the user, wherein each of the one or more sensing elements comprises at least one unique semiconductor identifier;

transmitting the at least one unique semiconductor identifier of the one or more sensing elements and the data concerning the one or more sensed characteristics to a data analytics engine;

attaching a plurality of unique biological identifiers associated with the user to the transmission of the at least one unique semiconductor identifier and the data concerning the one or more sensed characteristics;

verifying that the at least one unique semiconductor identifier of the one or more sensing elements and at least one of the plurality of unique biological identifiers are valid;

analyzing the data concerning the one or more sensed characteristics;

generating and transmitting a response based on the analysis;

determining at least one activity associated with the user to be anomalous;

dynamically altering which of the plurality of unique biological identifiers are referenced when verifying validity of the at least one of the plurality of unique biological identifiers;

generating a request for data from the integration device;

transmitting the request for data from the integration device to the data analytics engine with at least one unique semiconductor identifier corresponding to the integration device; and attaching the at least one of the plurality of unique biological identifiers associated with the user to the transmission of the request for data so that the data analytics engine can verify the validity of the at least one of the plurality of unique biological identifiers upon receipt of the request for data;

wherein the dynamically altering is automatically performed in response to the determination that the at least one activity is anomalous and is performed without notice to the user during the transmission of the at least one unique semiconductor identifier and the data concerning the one or more sensed characteristics.

18. The computer program product of claim 17, wherein the program instructions executable by the processor cause the processor to perform the method further comprising dynamically updating the at least one unique semiconductor identifier of the one or more sensing elements.

19. The computer program product of claim 17, wherein the program instructions executable by the processor cause the processor to perform the method further comprising:

verifying that the at least one unique semiconductor identifier corresponding to the integration device and the at least one biological identifier attached to the transmission of the request for data are valid; and using trends in positioning system data associated with the user to verify that the request for data from the integration device is valid.

20. The computer program product of claim 17, wherein analyzing the data concerning the one or more sensed characteristics comprises comparing the data concerning the one or more sensed characteristics to reference data, and determining whether the data concerning the one or more sensed characteristics falls outside of a range in the reference data.

* * * * *